United States Patent [19]

Yoneyoshi et al.

[11] Patent Number: 4,908,455

[45] Date of Patent: * Mar. 13, 1990

[54] METHOD FOR PRODUCING AN OPTICALLY ACTIVE AZOLYL-α β-UNSATURATED ALCOHOL

[75] Inventors: Yukio Yoneyoshi, Ohtsu; Gohfu Suzukamo, Ibaraki, both of Japan; Yoji Sakito, Montreal, Canada; Toshio Nishioka, Ashiya, Japan

[73] Assignee: Sumitomo Chemical Company, Limited, Osaka, Japan

[*] Notice: The portion of the term of this patent subsequent to Jul. 26, 2005 has been disclaimed.

[21] Appl. No.: 161,242

[22] Filed: Feb. 19, 1988

Related U.S. Application Data

[63] Continuation-in-part of Ser. No. 89,051, Aug. 24, 1987, abandoned, which is a continuation of Ser. No. 682,002, filed as PCT JP84/00162 on Apr. 3, 1984, published as WO85/04401 on Oct. 10, 1985, abandoned.

[51] Int. Cl.[4] .......................................... C07D 249/08
[52] U.S. Cl. .................................................. 548/268.4
[58] Field of Search ........................................ 548/262

[56] References Cited

U.S. PATENT DOCUMENTS 4,435,203  3/1984  Funoki et al. .................. 548/262
4,554,007  11/1985 Funoki et al. .................. 71/76
4,760,149  7/1988  Yoneyoshi et al. ............. 548/262

FOREIGN PATENT DOCUMENTS 0142566  5/1985  European Pat. Off. ........... 548/262

OTHER PUBLICATIONS

Mancilla et al., "Obtention de 3 Types de Derives, etc.", TL, 23, 1561, (1982).
Kyowa Hakko Kogyo KK, "Optically Active Beta--etc.", Abstract of Jap. Pat. Appln. 57-146786, (1982).
Itsuno et al. I, "A Symmetric Reduction of, etc.", J. Chem. Soc., Chem. Commun., (1983), 469.
Itsuno et al. II, "A Symmetric Synthesis Using, etc.", CA 100: 22184y, (1983).
Itsuno et al. III, "Asymmetric Reduction, etc.", CA 100: 67806u, (1984).
Chemical Abstracts, vol. 98, No. 13, 3/1983, p. 622, Abstract 107533b.
Journal of the Chemical Society, Perkin Transactions I, 1981, pp. 231-235, M. F. Grundon et al.
J. Org. Chem., vol. 37, No. 14, 2347, (1972).

Primary Examiner—Glennon H. Hollrah
Assistant Examiner—Patricia L. Morris
Attorney, Agent, or Firm—Stevens, Davis, Miller & Mosher

[57] ABSTRACT

The present invention relates to a method for producing optically active alcohol derivatives, which are useful as fungicides, herbicides or plant growth regulators, represented by the formula,

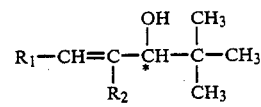

by carrying out the asymmetric reduction of a ketone compound represented by the formula,

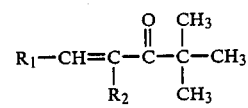

with a boron hydride-reducing agent modified with an optically active amino alcohol represented by the formula,

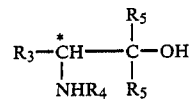

and also relates to the boron hydride type compound obtained by reacting the above optically active amino alcohol with a boron hydride compound and its production method.

9 Claims, No Drawings

METHOD FOR PRODUCING AN OPTICALLY ACTIVE AZOLYL-α β-UNSATURATED ALCOHOL

This application is a continuation-in-part of application Ser. No. 089,051, filed Aug. 24, 1987, which in turn is a continuation of application Ser. No. 682,002, filed as PCT JP84/00162 on Apr. 3, 1984, published as WO85/04401 on Oct. 10, 1985, both abandoned.

TECHNICAL FIELD

The present invention relates to a method for producing optically active α,β-unsaturated alcohols by the asymmetric reduction of ketone compounds. More particularly, it relates to a method for producing optically active alcohol derivatives represented by the formula (III),

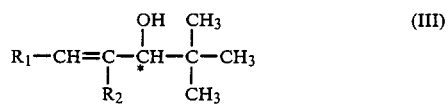

wherein $R_1$ represents a $C_3$-$C_8$ cycloalkyl group which may be substituted with a halogen atom, or a phenyl group which may be substituted with a halogen atom, or a $C_1$-$C_4$ alkyl group, a $C_1$-$C_4$ haloalkyl group, $R_2$ represents a 1,2,4-triazol-1-yl group and a mark * means an asymmetric carbon, by carrying out metric reduction of a ketone compound represented by the formula (I),

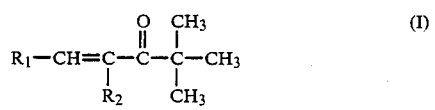

wherein $R_1$ and $R_2$ have the same meanings as above, with a boron hydride-reducing agent modified with an optically active amino alcohol represented by the formula (II),

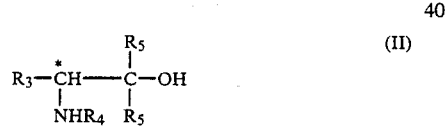

wherein $R_3$ represents a $C_1$-$C_8$ alkyl, $C_6$-$C_{10}$ aryl or $C_7$-$C_{11}$ aralkyl group, $R_4$ represents a hydrogen atom or a $C_1$-$C_6$ alkyl or $C_7$-$C_{16}$ aralkyl group, $R_5$ represents a hydrogen atom or a $C_1$-$C_{10}$ alkyl, $C_7$-$C_{16}$ aralkyl group or a $C_6$-$C_{18}$ aryl group which may be substituted with a $C_1$-$C_6$ alkyl or $C_1$-$C_6$ alkoxyl group, and a mark * has the same meaning as above, in the presence or absence of an acid; and also relates to the boron hydride type compound and its production method comprising reacting an optically active amino alcohol represented by the above formula (II) with a boron hydride compound.

BACKGROUND ART

The optically active alcohol derivative represented by the above formula (III), i.e. an azole type α,β-unsaturated alcohol derivative is known to be useful as an active ingredient for fungicides, plant growth regulators or herbicides, as represented for example by 1-(2,4-dichlorophenyl)-2-(1,2,4-triazol-1-yl)-4,4-dimethyl-1-penten-3-ol, 1-(4-chlorophenyl)-2-(1,2,4-triazol-1-yl)-4,4-dimethyl-1-penten-3-ol and 1-cyclohexyl-2-cyclohexyl-2-(1,2,4-triazol-1-yl)-4,4-dimethyl-1-penten-3-ol. And, it is also well known that there is a remarkable difference in the activity between the optical isomers, and that, for example with the foregoing 1-(2,4-dichlorophenyl)-2-(1,2,4-triazol-1-yl)-4,4-dimethyl-1-penten-3-ol and 1-(4-chlorophenyl)-2-(1,2,4-triazol-1-yl)-4,4-dimethyl-1-penten-3-ol, the (−)-isomer has a strong activity as fungicides, while the (+)-isomer has a strong activity as plant growth regulators and herbicides [Japanese Patent Application Kokai (Laid-open) Nos. 99575/1982 and 106669/1982].

For this reason, there is a great demand for the development of a method to produce either one of the (−)- or (+)-optical isomer according to intended uses and yet with a good efficiency in industry.

As the conventionally well-known common reducing agent for reducing the carbonyl group of ketone compounds into alcohol compounds, there are various reagents represented by lithium aluminum hydride and sodium borohydride. The reduction product produced when these reagents are used is an optically inactive, i.e. racemic compound, and when these reagents are used for the reduction of ketone compounds having an unsaturated bond, particularly α,β-conjugated unsaturated ketones like the material used in the method of the present invention, reduction of the double bond in addition to the carbonyl group is easy to occur, and besides there also comes out a possibility that the steric configuration correlated with the double bond is isomerized.

As the conventionally known asymmetric reduction method for the ketone compound represented by the above formula (I), there is a method in which for example a ketone compound represented by the formula (IV),

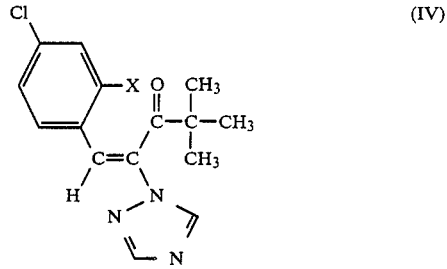

wherein X represents a hydrogen or chlorine atom, is reduced with an asymmetrically modified lithium aluminum hydride compound to obtain an optically active alcohol compound represented by the formula (V),

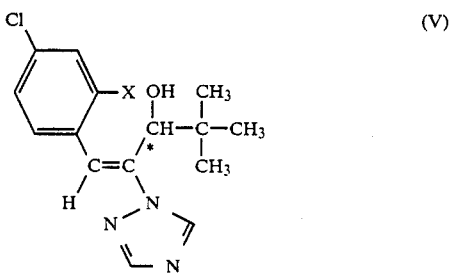

wherein X and a mark * have the same meanings as above, [Japanese Patent Application Kokai (Laid-open) Nos. 99575/1982 and 106669/1982].

Said method, however, may not always be said to be satisfactory in industry in the following points: (1) Since lithium aluminum hydride is used, there is a danger such as ignition by contact with moisture, and (2) in order to obtain an alcohol compound having a higher optical purity, additives such as N-substituted aniline are required in large amounts.

Also, in asymmetric reduction, the following methods are reported as a method for producing optically active alcohols using an asymmetrically modified boron hydride-reducing agent:

① A method of using sodium borohydride and the onium salt of optically active ephedrine [described in S. Colona, et al., J. Chem. Soc., Perkin Trans I, 371 (1978)], ② a method of using an optically active amine-borane complex [described in R. F. Borch, et al., J. Org. Chem. 37, 2347 (1972)], ③ a method of using an a-amino acid ester-borane complex [described in M. F. Grundon, et al., Tetrahedron Letters, 295 (1976)], and ④ a method of the asymmetric reduction of aromatic ketones with an optically active amino alcohol and borane [described in A. Hirao, et al., J. Chem. Soc. Chem. Comm., 315 (1981); S. Itsuno, et al., ibid. 469 (1983); and S. Itsuno, et al., J. Chem. Soc. Perkin Trans I, 1673 (1983)].

But, the methods ①, ② and ③ are too low in optical yield to say that they are a practical method. Also, the method ④ may not always be said to be satisfactory to carry it out in industry because, in order to attain high optical purity, borane of two times by mole, as converted to boron basis, as much as amino alcohol is required.

DISCLOSURE OF INVENTION

In view of the situation like this, the present inventors extensively studied a method for obtaining the optically active alcohol derivative represented by the formula (III) by the asymmetric reduction of the ketone compound represented by the above formula (I), and as a result, found that, by using a boron hydride-reducing agent modified with the optically active amino alcohol of the above formula (II), only the carbonyl group is selectively reduced into the objective optically active alcohol derivative with safety as well as good efficiency.

Next, the method of the present invention will be illustrated.

The optically active amino alcohol of the above formula (II) used in the method of the present invention can be produced, for example, by reacting the derivative of amino acids (e.g. commercially available optically active alanine, C-phenylglycine, phenylalanine, valine, leucine, isoleucine) with a Grignard reagent represented by the formula (VI),

$$R_5'MgY \qquad (VI)$$

wherein $R_5'$ represents a $C_1-C_{10}$ alkyl, $C_7-C_{16}$ group or a $C_6-C_{18}$ aryl group which may be substituted with a $C_1-C_6$ alkyl or $C_1-C_6$ alkoxyl group, and Y represents a halogen atom, or reducing the derivative of the foregoing amino acids [A. Mckenzie, et al., J. Chem. Soc., 123, 79 (1923); A. Mckenzie, et al., Chem. Ber., 62, 288 (1920); A. Mckenzie, et al., J. Chem. Soc., 779 (1926); and S. Hayashi, et al., Chem. Pharm. Bull., 17, 145 (1969)].

In the formula (II), $R_3$ is a substituent resulting from the derivative of the foregoing amino acids, and its specific example includes a methyl, isopropyl, isobutyl, sec-butyl, tert-butyl, phenyl and benzyl groups. Specific examples of $R_4$ include a hydrogen atom, a methyl, ethyl, n-propyl and isopropyl groups. Specific examples of $R_5$ include a phenyl, o-toluyl, m-toluyl, p-toluyl, 2,5-xylyl, o-methoxyphenyl, m-methoxyphenyl, p-methoxyphenyl, o-ethoxyphenyl, benzyl and methyl groups.

In the present invention, the halogen atom represents fluorine atom, chlorine atom or bromine atom.

Next, reference will be made to a method for producing the boron hydride-reducing agent modified with the optically active amino alcohol (hereinafter referred to as present reducing agent) which is obtained by reacting the optically active amino alcohol represented by the formula (II) or its salt with an acid with a boron hydride compound.

The present reducing agent, when the boron hydride compound is a metal borohydride, is obtained by reacting a salt, as obtained from the optically active amino alcohol represented by the formula (II) and an acid, with the metal borohydride in a solvent, or when the boron hydride compound is a borane, it is obtained by directly reacting the optically active amino alcohol represented by the formula (II) with the borane in a solvent. As the foregoing acid which is a material for producing the salt of the optically active amino alcohol, there are given mineral acids (e.g. hydrochloric acid, sulfuric acid, nitric acid, phosphoric acid), carboxylic acids (e.g. acetic acid), organic sulfonic acids (e.g. p-toluenesulfonic acid) and the like. Said salt may be used as such or may be produced, in situ, from the optically active amino alcohol and the acid in the reaction system for producing the present reducing agent.

As the metal borohydride described above, there are given for example sodium borohydride, potassium borohydride, lithium borohydride, zinc borohydride, etc. But, the object of the present invention can sufficiently be achieved by using easily available sodium borohydride. As the borane, diborane, borane-tetrahydrofuran complex, borane-dimethyl sulfide complex, etc. may be used.

In production of the present reducing agent, the molar ratio of the boron hydride compound to the optically active amino alcohol is, when said compound is a metal borohydride, generally 0.3:1 to 2:1, preferably 0.3:1 to 1.2:1, more preferably 1 to 1, as converted to boron basis, and when said compound is a borane, said molar ratio is generally 0.3:1 to 1.2:1, preferably 1 to 1.

The solvent used in producing the present reducing agent is not particularly limited, so long as it does not take part in the reaction. For example, however, there are given aromatic hydrocarbons (e.g. benzene, toluene, xylene, chlorobenzene), halogenated hydrocarbons (e.g. methylene chloride, 1,2-dichloroethane, chloroform, carbon tetrachloride), and mixtures thereof. When the metal borohydride is used, in order to solve it, for example dimethyl sulfoxide, diglyme, dimethylformamide, 1,3-dimethyl-2-imidazolidinone or the like may be used in combination. The reaction temperature is generally within a range of $-78°$ to $100°$ C., preferably $-40°$ to $100°$ C. The reaction is generally carried out in an inert gas atmosphere such as nitrogen, argon, etc.

The present reducing agent thus obtained may be used for the subsequent reduction after separated from the reaction solution, but generally, it is used as the solution without being separated therefrom.

Next, reference will be made to a method for producing the optically active alcohol derivative of the above formula (III) by reduction of the ketone compound represented by the above formula (I) using the present reducing agent thus obtained.

The amount of the present reducing agent used in the reduction is not less than 0.5 mole, generally within a range of 1 to 5 moles, as converted to boron basis, based on 1 mole of the ketone compound, and even the range of 1 to 2 moles can sufficiently achieve the object.

Also, the solvent used in the foregoing reduction is not particularly limited, so long as it is an inactive solvent. Preferably, however, organic solvents such as aromatic hydrocarbons (e.g. benzene, toluene, xylene, chlorobenzene), halogenated hydrocarbons (e.g. methylene chloride, 1,2-dichloroethane, chloroform, carbon tetrachloride), ethers (e.g. diethyl ether, tetrahydrofuran, dioxane, diglyme) and mixtures thereof are used. Also, the solvent used in producing the present reducing agent may be used as it is or in mixture with the solvents described above. The reduction is carried out in an inert gas atmosphere as described above. The temperature of the reduction is generally within a range of $-30°$ to $100°$ C., and industrially within a range of $-10°$ to $50°$ C.

The foregoing reduction may be carried out in the presence of an acid, and particularly when sodium borohydride is used as a material for the present reducing agent, isomerization between the E form and Z form of the ketone compound represented by the above formula (I) is inhibited, whereby the yield of the objective optically active alcohol derivative can be increased. As the acid, there are given for example Lewis acids (e.g. titanium tetrachloride, boron trifluoride etherate, aluminum chloride), carboxylic acids (e.g. acetic acid, chloroacetic acid, propionic acid), and mineral acids (e.g. hydrochloric acid, sulfuric acid, phosphoric acid). The molar ratio of these acids to the ketone compound is generally within a range of 0.01:1 to 1:1, preferably 0.01:1 to 0.5:1.

After the reduction is carried out in this way, the aqueous solution of a mineral acid (e.g. hydrochloric acid, sulfuric acid) is generally added to the reaction solution, the organic layer is separated from the aqueous layer, washed with water and dried, and then the organic solvent is removed by evaporation. By this procedure, the objective aforementioned optically active alcohol derivative represented by the formula (III) is obtained in a high yield.

The optical purity is obtained by measuring the optical rotation of the product obtained, or directly measuring the enantiomer ratio by high-performance liquid chromatography with optically active packing materials.

Hereupon, the optically active amino alcohol used can easily be recovered, with its steric configuration maintained, by adding an aqueous alkali solution to the aqueous layer after the reaction and extracting with an organic solvent. The recovered optically active amino alcohol can be re-used.

BEST MODE FOR CARRYING OUT THE INVENTION

EXAMPLE 1

In a nitrogen atmosphere, 0.551 g (1.8 mmoles) of (S)-2-amino-1,1-diphenyl-4-methylpentan-1-ol hydrochloride was suspended in 5 ml of 1,2-dichloroethane, and after cooling to $-20°$ C., a solution of 0.0681 g (1.8 mmoles) of sodium borohydride in 1 ml of dimethylformamide was added. The temperature of the suspension was raised from $-20°$ C. to room temperature over 2 hours. Thereafter, a solution of 0.348 g (1.2 mmoles) of (E)-1-(4-chlorophenyl)-2-(1,2,4-triazol-1-yl)-4,4-dimethyl-1-penten-3-one in 4 ml of 1,2-dichloroethane was added to this suspension at room temperature, and stirring was carried out for 48 hours. Thereafter, 6 ml of 2N hydrochloric acid was added and stirring was carried out for 2 hours. After removing the intermediate layer by filtration, the organic layer was washed with water and concentrated under reduced pressure, and the residue was purified on a column packed with 2 g of silica gel with chloroform as a developing solvent to obtain 0.35 g of (+)-(E)-1-(4-chlorophenyl)-2-(1,2,4-triazol-1-yl)-4,4-dimethyl-1-penten-3-ol as a crystal. By gas-chromatographic analysis, it was found that the conversion was 96.3%, and the composition of the product was: E-form alcohol, 78.9%; Z-form alcohol, 20.3%; and saturated alcohol, 0.8% (said alcohol means a product obtained by hydrogenation of both the carbonyl group and the double bond contained in the $\alpha,\beta$-unsaturated ketone used as a material). By high-performance liquid-chromatographic analysis using an optically active column, it was found that the enantiomer ratio of the produced E-form alcohol was: (+)-isomer, 86.1% and (−)-isomer, 13.9%. The optical yield was 72.2%.

EXAMPLES 2 to 5

Reaction was carried out according to Example 1 using (S)-2-amino-1,1-diphenylpropan-1-ol hydrochloride, (S)-2-amino-1,1-diphenyl-3-methylbutan-1-ol hydrochloride, (R)-2-amino-1,1-diphenyl-3-phenylpropan-1-ol acetate and (S)-2-amino-1,1-di-(2'-methoxyphenyl)-4-methylpentan-1-ol acetate in place of (S)-2-amino-1,1-diphenyl-4-methylpentan-1-ol hydrochloride, to obtain the (+)-isomer and (-)-isomer of (E)-1-(4-chlorophenyl)-2-(1,2,4-triazol-1-yl)-4,4- dimethyl-1-penten-3-ol. The results obtained were summarized in Table 1.

TABLE 1

| Example No. | Optically active amino alcohol | Reaction time (hr) |
| --- | --- | --- |
| 1 | 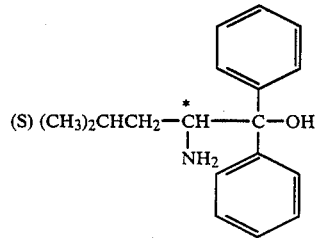 (S) (CH$_3$)$_2$CHCH$_2$—CH—C—OH with NH$_2$ | 48 |
| 2 | 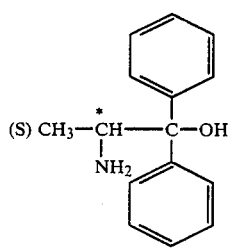 (S) CH$_3$—CH—C—OH with NH$_2$ | 21 |

TABLE 1-continued

| | Reaction product | |
|---|---|---|
| 3 | (S) (CH₃)₂CH—*CH(NH₂)—C(OH)(C₆H₅)₂ | 68 |
| 4 | (R) C₆H₅—CH₂—*CH(NH₂)—C(OH)(C₆H₅)₂ | 67 |
| 5 | (S) (CH₃)₂CHCH₂—*CH(NH₂)—C(OH)(2-OCH₃-C₆H₄)₂ | 23 |

| Conversion (%) | Reaction product E-form alcohol/Saturated alcohol/Z-form** alcohol | Enantiomer ratio (−/+) of E-form alcohol | Optical yield of E-form alcohol (%) |
|---|---|---|---|
| 96.3 | 78.9/0.8/20.3 | 13.9/86.1 | 72.2 |
| 60.0 | 82.6/4.8/12.6 | 20.4/79.6 | 59.2 |
| 84.6 | 88.2/2.9/8.9 | 14.7/85.3 | 70.6 |
| 79.6 | 79.8/5.8/14.4 | 81.2/18.8 | 62.4 |
| 70.7 | 82.3/4.6/13.1 | 15.3/84.7 | 69.4 |

**Z-form alcohol is produced through isomerization of the ketone, a material, to the Z form, followed by reduction of the carbonyl group.

EXAMPLE 6

Reaction was carried out in the same manner as in Example 1 except that the hydrochloride of (S)-2-amino-1,1-diphenyl-4-methylpentan-1-ol was replaced by the acetate thereof, the amount of sodium borohydride used was 0.075 g (1.98 mmoles), and that the reaction was carried out for 91 hours with addition of 0.0162 g (0.27 mmole) of acetic acid to (E)-1-(4-chlorophenyl)-2-(1,2,4-triazol-1-yl)-4,4-dimethyl-1-penten-3-one, to obtain (+)-(E)-1-(4-chlorophenyl)-2-(1,2,4-triazol-1-yl)-4,4-dimethyl-1-penten-3-ol. The conversion was 100%, and the composition of the product was: E-form alcohol, 90.3%; Z-form alcohol, 6.3%; and saturated alcohol, 3.4%. The enantiomer ratio of the E-form alcohol was: (+)-isomer, 86.5% and (−)-isomer, 13.5%. The optical yield was 73%.

EXAMPLE 7

In a nitrogen atmosphere, 3.5 ml of a chloroform solution containing 0.233 g (0.86 mmole) of (S)-2-amino-1,1-diphenyl-4-methylpentan-1-ol was added at −60° C. to 0.87 ml (0.87 mmole) of a 1.0M borane-tetrahydrofuran solution, and the temperature of the resulting solution was raised to room temperature over 2 hours. Thereafter, 2 ml of a chloroform solution containing 0.164 g (0.57 mmole) of (E)-1-(4-chlorophenyl)-2-(1,2,4-triazol-1-yl)-4,4-dimethyl-1-penten-3-one was added to this solution at room temperature, and stirring was carried out for 24 hours. After-treatment was carried out in the same manner as in Example 1 to obtain 0.164 g of (+)-(E)-1-(4-chlorophenyl)-2-(1,2,4-triazol-1-yl)-4,4-dimethyl-1-penten-3-ol. The conversion was 87.0%, and the composition of the product was: E-form alcohol, 97.3% and Z-form alcohol, 2.7%. The enantiomer ratio of the E-form alcohol was: (+)-isomer, 87.2% and (−)-isomer 12.8%.

EXAMPLE 8

To 3 ml of a chloroform solution containing 0.117 g (0.43 mmole) of (S)-2-amino-1,1-diphenyl-4-methylpentan-1-ol was added 0.052 g (0.87 mmole) of acetic acid, and the mixture was cooled to −60° C. Thereafter, 0.5 ml of a dimethylformamide solution containing 0.033 g (0.87 mmole) of sodium borohydride was added, and the temperature of the mixture was raised to room temperature over 2 hours. To this suspension was added 3 ml of a methylene chloride solution containing 0.084 g (0.29 mmole) of (E)-1-(4-chlorophenyl)-2-(1,2,4-triazol-1-yl)-4,4-dimethyl-1-penten-3-one, and stirring was carried out at room temperature for 17 hours. The same treatment as in Example 1 was applied to obtain (+)-(E)-1-(4-chlorophenyl)-2-(1,2,4-triazol-1-yl)-4,4-dimethyl-1-penten-3-ol. The conversion was 53.7%, and the composition of the product was: E-form alcohol, 85.4% and Z-form alcohol, 14.5%. The enantiomer ratio of the E-form alcohol was: (+)-isomer, 86.0% and (−)-isomer, 14.0%.

EXAMPLES 9 to 12

Reaction was carried out in the same manner as in Example 1 except that (E)-1-(4-chlorophenyl)-2-(1,2,4-triazol-1-yl)-4,4-dimethyl-1-penten-3-one was replaced by (E)-1-(2,4-dichlorophenyl)-2-(1,2,4-triazol-1-yl)-4,4-dimethyl-1-penten-3-one, and that (S)-2-amino-1,1-diphenyl4-methylpentan-1-ol hydrochloride was replaced by (S)-2-amino-1,1-diphenylpropan-1-ol hydrochloride, (S)-2-amino-1,1-diphenyl-3-methylbutan-1-ol hydrochloride, (S)-2-amino-1,1-dibenzylpropan-1-ol hydrochloride and (S)-2-amino-3-phenylpropan-1-ol hydrochloride, to obtain (+)-(E)-1-(2,4-dichlorophenyl)-2-(1,2,4-triazol-1-yl)-4,4-dimethyl-1-penten-3-ol. The results were summarized in Table 2.

TABLE 2

| Example No. | Optically active amino alcohol | Reaction time (hr) |
|---|---|---|
| 9 | (S) CH₃—*CH(NH₂)—C(OH)(C₆H₅)₂ | 24 |

TABLE 2-continued

| # | Structure | Value |
|---|---|---|
| 10 | (S) (CH₃)₂CH—*CH—C(OH)(C₆H₅)₂ with NH₂ | 24 |
| 11 | (S) CH₃—*CH(NH₂)—C(OH)(CH₂C₆H₅)(CH₂—) | 24 |
| 12 | (S) C₆H₅—CH₂—*CH(NH₂)—CH₂—OH | 93 |

| Conversion (%) | Reaction product E-form alcohol/Saturated alcohol/Z-form alcohol | Enantiomer ratio (−/+) of E-form alcohol | Optical yield of E-form alcohol (%) |
|---|---|---|---|
| 96.8 | 96.8/0.6/0.6 | 24.5/75.5 | 51.0 |
| 80.4 | 96.4/2.5/1.1 | 22.9/77.1 | 54.2 |
| 90.2 | 97.9/0.4/1.3 | 29.7/70.3 | 40.6 |
| 89.6 | 100/0/0 | 68.5/31.5 | 37.0 |

EXAMPLE 13

In a nitrogen atmosphere, 0.275 g (0.90 mmole) of (S)-2-amino-1,1-diphenyl-4-methylpentan-1-ol hydrochloride was suspended in 5 ml of 1,2-dichloroethane, and after cooling to −20° C., a solution of 0.034 g (0.90 mmole) of sodium borohydride in 0.5 ml of dimethylformamide was added. The temperature of the suspension was then raised from −20° C. to room temperature over 2 hours. Thereafter, a solution of 157 mg (0.60 mmole) of (E)-1-cyclohexyl-4,4-dimethyl-2-(1,2,4-triazol-1-yl)-1-penten-3-one in 2 ml of 1,2-dichloroethane was added dropwise to this suspension at room temperature, and stirring was carried out for 24 hours. To this reaction solution was added 6 ml of 2N hydrochloric acid, and after removing liberated (S)-2-amino-1,1-diphenyl-4-methylpentan-1-ol hydrochloride by filtration, the organic layer was washed with water and concentrated under reduced pressure. The residue was purified by column chromatography on silica gel to obtain 0.158 g of (−)-(E)-cyclohexyl-4,4-dimethyl-2-(1,2,4-triazol-1-yl)-1-penten-3-ol. The conversion was 93.7%, and the composition of the product was: E-form alcohol, 95.7% and Z-form alcohol, 4.3%. The enantiomer ratio of the E-form alcohol was: (+)-isomer, 18.8% and (−)-isomer, 81.2%.

EXAMPLE 14

In a nitrogen atmosphere, a solution of 0.485 g (1.8 mmoles) of (S)-2-amino-1,1-diphenyl-4-methylpentan-1-ol in 5 ml of 1,2-dichloroethane was added dropwise at −78° C. to a solution comprising 1.8 ml (1.8 mmoles) of 1.00M borane-tetrahydrofuran solution and 2 ml of 1,2-dichloroethane, and the temperature of the mixture was raised from −78° C. to room temperature over about 2 hours. Thereafter, a solution of 0.31 g (1.2 mmoles, E/Z=99.9/0.1) of (E)-1-cyclohexyl-4,4-dimethyl-2-(1,2,4-triazol-1-yl)-1-penten-3-one in 3 ml of 1,2-dichloroethane was added dropwise to this solution, and stirring was carried out for 24 hours. The reaction product was decomposed with addition of 6 ml of 2N hydrochloric acid to the solution, and after removing (S)-2-amino-1,1-diphenyl-4-methylpentan-1-ol hydrochloride by filtration, the organic layer was washed with water and concentrated under reduced pressure. The residue was purified on a column packed with 2 g of silica gel with chloroform as a developing solvent to obtain (−)-(E)-1-cyclohexyl-4,4-dimethyl-2-(1,2,4-triazol-1-yl)-1-penten-3-ol. The conversion was 100%, and the composition of the product was: E-form alcohol, 99.1% and Z-form alcohol, 0.9%. The enantiomer ratio of the E-form alcohol was: (+)-isomer, 16.3% and (−)-isomer, 83.7%.

EXAMPLE 15

306 Milligrams (1 mmole) of (S)-2-amino-1,1-diphenyl-4-methylpentan-1-ol hydrochloride was suspended in 3.5 ml of deutero chloroform, and the suspension was cooled to −20° C. After adding 1.0 ml of a dimethylformamide solution containing 38 mg (1 mmole) of sodium borohydride, the temperature of the suspension was raised to room temperature over 2 hours.

$^{11}$B NMR (CDCl₃DMF, 200 MHz; standard, BF₃.Et₂O) was as follows: δ(ppm)=−20.0, −12.4, −2.6, +4.9.

EXAMPLE 16

In a nitrogen atmosphere, 0.2626 g (0.90 mmole) of (S)-2-amino-1,1-diphenyl-3-methylbutan-1-ol hydrochloride was suspended in 2.5 ml of 1,2-dichloroethane, and after cooling to −20° C., a solution of 0.0341 g (0.90 mmole) of sodium borohydride in 0.5 ml of dimethylformamide was added. The temperature of the suspension was then raised from −20° C. to room temperature over 2 hours. Thereafter, a solution of 157 mg (0.60 mmole) of (E)-1-cyclohexyl-4,4-dimethyl-2-(1,2,4-triazol-1-yl)-1-penten-3-one in 2 ml of 1,2-dichloroethane was added dropwise to this suspension at room temperature, and stirring was carried out for 24 hours. To this reaction solution was added 6 ml of 10% hydrochloric acid, and after removing liberated (S)-2-amino-1,1-diphenyl-3-methylbutan-1-ol hydrochloride by filtration, the organic layer was washed with water and concentrated under reduced pressure to obtain 0.156 g of crude (−)-(E)-1-cyclohexyl-4-4-dimethyl-2-(1,2,4-triazol-1-yl)-1-penten-3-ol.

The conversion was 98.6%, and the composition of the product was: E-form alcohol, 99.3% and Z-form alcohol, 0.7%. The enantiomer ratio of the E-form alcohol was: (+)-isomer, 17.2% and (−)-isomer, 82.8%.

EXAMPLES 17 to 21

Experiments were carried out according to the method of Example 16 above except that the amount of sodium borohydride used was varied to vary the Molar Ratio to the used optically active amino-alcohol.

The results obtained in Examples 17-21 are summarized in the following Table 3:

TABLE 3

| | | Composition of reaction product | | | |
|---|---|---|---|---|---|
| No. | Sodium borohydride (mmole) (Molar Ratio) | Conversion (%) | E-form alcohol (%) | Z-form alcohol (%) | Enantiomer ratio of E-form alcohol (+)/(−) | Optical yield of E-form (%) |
| 17 | 0.99 (1.1) | 99.8 | 99.2 | 0.8 | 17.6/82.4 | 64.8 |
| 18 | 0.90 (1.0) | 98.6 | 99.3 | 0.7 | 17.2/82.8 | 65.6 |
| 19 | 0.63 (0.7) | 94.8 | 99.3 | 0.7 | 17.4/82.6 | 65.2 |
| 20 | 0.45 (0.5) | 93.9 | 99.5 | 0.5 | 18.0/82.0 | 64.0 |
| 21 | 0.27 (0.3) | 57.4 | 99.4 | 0.6 | 18.0/82.0 | 64.0 |

*Molar Ratio: A ratio of sodium borohydride to (S)—2-amino-1, 1-diphenyl-3-methylbutan-1-ol.

EXAMPLE 22

In a nitrogen atmosphere, a solution of 0.230 g (0.90 mmole) of (S)-2-amino-1,1-diphenyl-3-methylbutan-1-ol in 2.5 ml of 1,2-dichloroethane was added dropwise at −78° C. to a solution comprising 1.29 ml (0.90 mmole) of 0.70M borane-tetrahydrofuran solution and 1 ml of 1,2-dichloroethane, and the temperature of the mixture was raised from −78° C. to room temperature over about 2 hours. Thereafter, a solution of 0.157 g (0.6 mmole, E/Z=99.9/0.1) of (E)-1-cyclohexyl-4,4-dimethyl-2-(1,2,4-triazol-1-yl)-1-penten-3-one in 2.5 ml of 1,2-dichloroethane was added dropwise to this solution, and stirring was carried out for 24 hours. The reaction product was decomposed with addition of 6 ml of 10% hydrochloric acid to the solution, and after removing (S)-2-amino-1,1-diphenyl-3-methylbutan-1-ol hydrochloride by filtration, the organic layer was washed with water and concentrated under reduced pressure to obtain crude (−)-(E)-1-cyclohexyl-4,4-dimethyl-2-(1,2,4-triazol-1-yl)-1-penten-3-ol.

The conversion was 8.3%, and the composition of the product was: E-form alcohol, 99.7% and Z-form alcohol, 0.3%. The enantiomer ratio of the E-form alcohol: (+)-isomer, 19.5% and (−)-isomer, 80.5%.

EXAMPLES 23 to 26

Experiments were carried out according to the method of Example 22 above except that the used amount of borane-tetrahydrofuran was varied to vary the Molar Ratio to the used optically active amino-alcohol.

The results obtained in Examples 23-26 are summarized in the following Table 4:

TABLE 4

| | | Composition of reaction product | | | |
|---|---|---|---|---|---|
| No. | Borane-tetrahydrofuran (mmole) (Molar Ratio)* | Conversion (%) | E-form alcohol (%) | Z-form alcohol (%) | Enantiomer ratio of E-form alcohol (+)/(−) | Optical yield of E-form (%) |
| 23 | 0.99 (1.1) | 77.8 | 99.7 | 0.3 | 20.7/79.3 | 58.6 |
| 24 | 0.90 (1.0) | 83.8 | 99.7 | 0.3 | 19.5/80.5 | 61.0 |
| 25 | 0.63 (0.7) | 99.7 | 99.8 | 0.2 | 20.3/79.7 | 59.4 |
| 26 | 0.27 (0.3) | 87.0 | 99.8 | 0.2 | 20.8/79.2 | 58.4 |

*Molar Ratio: A ratio of borane-tetrahydrofuran to (S)-2-amino-1,1-diphenyl-3-methylbutan-1-ol.

We claim:

1. A method for producing optically active alcohol derivatives represented by the formula (III)

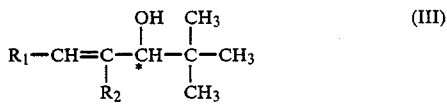

wherein $R_1$ represents a $C_3$–$C_8$ cycloalkyl, or a phenyl which may be substituted with a halogen, or a $C_1$–$C_4$ haloalkyl, $R_2$ represents 1,2,4-triazol-1-yl and the mark * means an asymmetric carbon, comprising asymmetrically reducing a ketone compound represented by the formula (I),

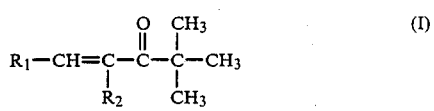

wherein $R_1$ and $R_2$ have the same meanings as above, with boron hydride reducing agent modified with an optically active amino alcohol represented by the formula (II),

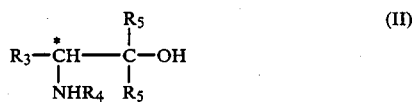

wherein said modified boron hydride reducing agent is obtained by reacting a metal borohydride with a salt of the optically active amino alcohol with acid or by reacting a borane with the optically active amino alcohol, each in a molar ratio of a range from 0.3:1 to 1.2:1 and wherein $R_3$ represents $C_1$–$C_8$ alkyl or $C_7$–$C_{11}$ aralkyl, $R_4$ represents a hydrogen, $R_5$ represents a hydrogen or $C_7$–$C_{16}$ aralkyl or a phenyl which may be substituted with $C_1$–$C_6$ alkoxy, and the mark * has the same meaning as above, in the presence or absence of an acid.

2. A method according to claim 1, wherein the metal borohydride is sodium borohydride.

3. A method according to claim 1, wherein the asymmetric reduction is carried out in the presence of an acid.

4. A method according to claim 3, wherein the acid is a Lewis acid, organic acid or mineral acid.

5. A method according to claim 3, wherein the molar ratio of the acid to the ketone compound is 0.01:1 to 0.5:1.

6. A method according to any one of claims 1, 2, 3, 4, or 5, wherein, in the above formula (II), $R_4$ is a hydrogen and $R_5$ is a phenyl which may be substituted with a $C_1$–$C_6$ alkoxy.

7. A method according to any one of claims 1, 2, 3, 4 or 5, wherein, in the above formula (II), $R_4$ is a hydrogen and $R_5$ is a phenyl, or 2-methoxyphenyl.

8. A method according to any one of claims 1, 2, 3, 4 or 5, wherein in the above formula (II), $R_3$ is a methyl, isopropyl, isobutyl or benzyl.

9. A method according to any one of claims 1, 2, 3, 4 or 5, wherein, in the above formulas (I) and (III), $R_1$ is a 2,4-dichlorophenyl, 4-chlorophenyl or cyclohexyl.

* * * * *